(12) United States Patent
Walters et al.

(10) Patent No.: US 7,931,657 B2
(45) Date of Patent: Apr. 26, 2011

(54) APPARATUS AND METHOD FOR MANIPULATING A FLEXIBLE STRAND AND SOFT TISSUE REPLACEMENT DURING SURGERY

(75) Inventors: Troy Walters, Plymouth, IN (US); Jason Meridew, Columbia City, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1213 days.

(21) Appl. No.: 11/384,989

(22) Filed: Mar. 20, 2006

(65) Prior Publication Data

US 2006/0173466 A1 Aug. 3, 2006

Related U.S. Application Data

(62) Division of application No. 10/066,519, filed on Jan. 31, 2002, now Pat. No. 7,033,364.

(51) Int. Cl.
*A61B 17/60* (2006.01)
*A61F 2/00* (2006.01)

(52) U.S. Cl. ........................................................ 606/98

(58) Field of Classification Search .................. 606/53, 606/86 R, 87, 96–99, 103; 623/13.11–13.14, 623/13.17–13.19, 13.2
See application file for complete search history.

(56) References Cited

U.S. PATENT DOCUMENTS

| | | | |
|---|---|---|---|
| 2,695,607 A | 11/1954 | Hipps et al. | |
| 3,871,379 A | 3/1975 | Clarke | |
| D249,705 S | 9/1978 | London | |
| 4,257,411 A | 3/1981 | Cho | |
| 4,535,768 A | 8/1985 | Hourahane et al. | |
| 4,922,897 A | 5/1990 | Sapega et al. | |
| 4,985,032 A | 1/1991 | Goble | |
| 4,998,937 A | 3/1991 | Grimes | |
| 5,004,474 A | 4/1991 | Fronk et al. | |
| 5,030,219 A | 7/1991 | Matsen, III et al. | |
| 5,098,435 A | 3/1992 | Stednitz et al. | |
| 5,108,396 A | 4/1992 | Lackey et al. | |
| 5,112,336 A | 5/1992 | Krevolin et al. | |
| 5,129,902 A | 7/1992 | Goble et al. | |
| 5,201,744 A | 4/1993 | Jones | |
| 5,234,434 A | 8/1993 | Goble et al. | |
| 5,234,444 A | 8/1993 | Christoudias | |
| 5,257,996 A | 11/1993 | McGuire | |
| 5,266,075 A | 11/1993 | Clark et al. | |
| 5,300,077 A | 4/1994 | Howell | |
| 5,350,380 A | 9/1994 | Goble et al. | |
| 5,354,300 A | 10/1994 | Goble et al. | |
| 5,356,413 A | 10/1994 | Martins et al. | |
| 5,393,302 A | 2/1995 | Clark et al. | |
| 5,397,356 A | 3/1995 | Goble et al. | |
| D357,534 S | 4/1995 | Hayes | |
| 5,423,823 A | 6/1995 | Schmieding | |
| 5,431,651 A | 7/1995 | Goble | |
| 5,437,677 A | 8/1995 | Shearer et al. | |

(Continued)

FOREIGN PATENT DOCUMENTS

EP 1 360 949 11/2003

(Continued)

*Primary Examiner* — Anu Ramana
(74) *Attorney, Agent, or Firm* — Harness, Dickey

(57) ABSTRACT

An system and method for performing a surgery, such as an anterior-cruciate-ligament replacement surgery, where a flexible strand insertion rod can co-operate with a U-Guide apparatus to insert a flexible strand into a tunnel formed in a bone portion. A soft tissue replacement can be affixed to one end of the flexible strand and pulled over a retaining member with the other end of the flexible strand.

39 Claims, 5 Drawing Sheets

U.S. PATENT DOCUMENTS

| | | |
|---|---|---|
| 5,454,365 A | 10/1995 | Bonutti |
| 5,562,671 A | 10/1996 | Goble et al. |
| 5,601,562 A | 2/1997 | Wolf et al. |
| 5,643,273 A | 7/1997 | Clark |
| 5,674,224 A | 10/1997 | Howell et al. |
| 5,849,013 A | 12/1998 | Whittaker et al. |
| 5,891,150 A | 4/1999 | Chan |
| 5,895,425 A | 4/1999 | Grafton et al. |
| 5,918,604 A | 7/1999 | Whelan |
| 5,931,839 A | 8/1999 | Medoff |
| 6,039,739 A | 3/2000 | Simon |
| 6,066,173 A | 5/2000 | McKernan et al. |
| 6,110,211 A | 8/2000 | Weiss |
| 6,113,604 A | 9/2000 | Whittaker et al. |
| 6,132,433 A | 10/2000 | Whelan |
| 6,231,611 B1 | 5/2001 | Mosseri |
| 6,306,138 B1 | 10/2001 | Clark et al. |
| 6,325,804 B1 | 12/2001 | Wenstrom, Jr. et al. |
| 6,342,056 B1 | 1/2002 | Mac-Thiong et al. |
| 6,371,124 B1 | 4/2002 | Whelan |
| 6,375,684 B1 | 4/2002 | Kriek |
| 6,379,384 B1 | 4/2002 | McKernan et al. |
| 6,494,913 B1 | 12/2002 | Huebner |
| 6,497,726 B1 | 12/2002 | Carter et al. |
| 6,517,546 B2 | 2/2003 | Whittaker et al. |
| 6,537,319 B2 | 3/2003 | Whelan |
| 6,562,071 B2 | 5/2003 | Jarvinen |
| 6,589,281 B2 | 7/2003 | Hyde, Jr. |
| 6,673,115 B2 | 1/2004 | Resch et al. |
| 6,712,823 B2 | 3/2004 | Grusin et al. |
| 6,712,849 B2 | 3/2004 | Re et al. |
| 6,733,529 B2 | 5/2004 | Whelan |
| 6,752,830 B1 | 6/2004 | Goble et al. |
| 2001/0047210 A1 | 11/2001 | Wolf |
| 2001/0053934 A1 | 12/2001 | Schmieding |
| 2002/0019635 A1 | 2/2002 | Wenstrom, Jr. et al. |
| 2002/0087160 A1 | 7/2002 | Clark et al. |
| 2002/0099381 A1 | 7/2002 | Maroney |
| 2002/0111689 A1 | 8/2002 | Hyde, Jr. |
| 2002/0111690 A1 | 8/2002 | Hyde |
| 2002/0133153 A1 | 9/2002 | Hyde, Jr. |
| 2002/0138148 A1 | 9/2002 | Hyde, Jr. |
| 2002/0138149 A1 | 9/2002 | Hyde, Jr. |
| 2003/0097179 A1 | 5/2003 | Carter et al. |
| 2003/0163202 A1 | 8/2003 | Lakin |
| 2004/0092936 A1 | 5/2004 | Miller et al. |

FOREIGN PATENT DOCUMENTS

| | | |
|---|---|---|
| FR | 2 684 543 | 6/1993 |

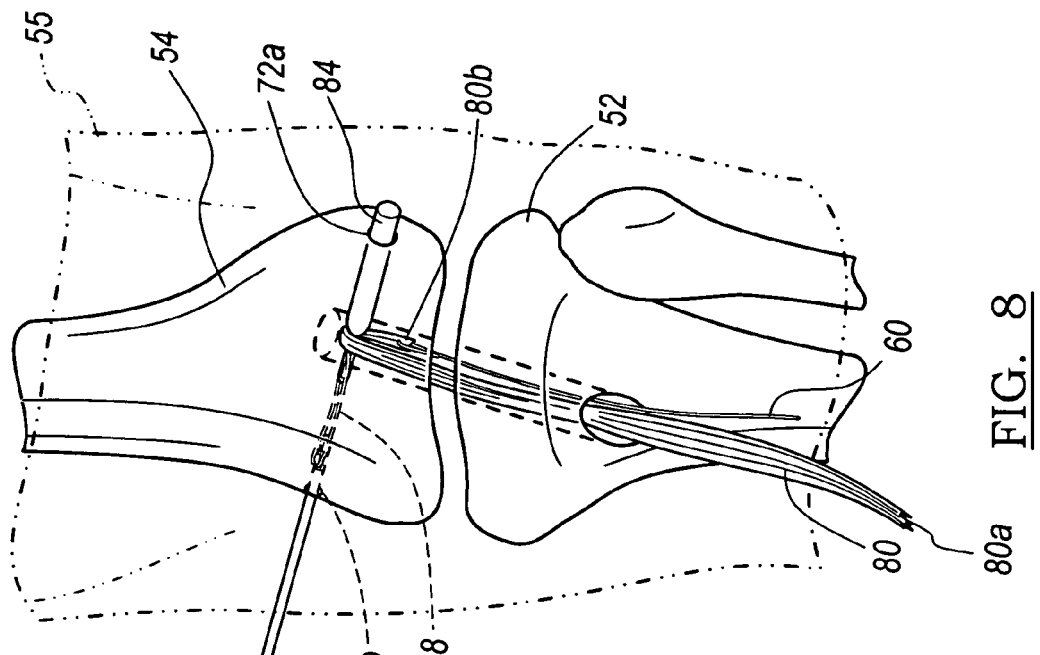
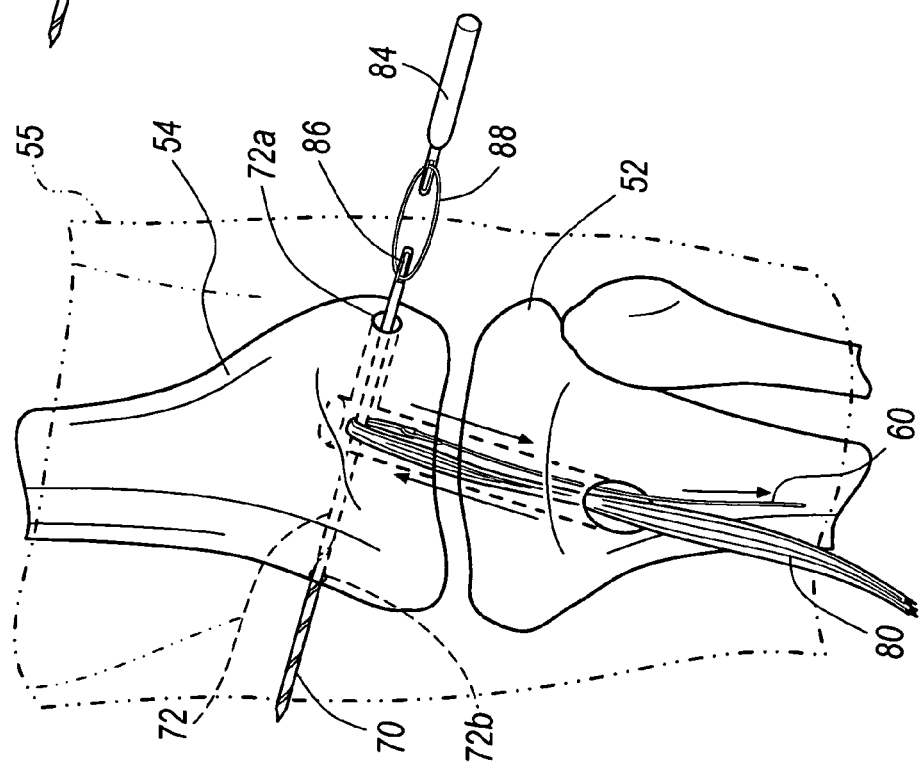

APPARATUS AND METHOD FOR
MANIPULATING A FLEXIBLE STRAND AND
SOFT TISSUE REPLACEMENT DURING
SURGERY

CROSS-REFERENCE TO RELATED APPLICATIONS

This application is a divisional of U.S. patent application Ser. No. 10/066,519 filed on Jan. 31, 2002. The disclosure of the above application is incorporated herein by reference.

FIELD

The present teachings relate to soft tissue replacement fixation. More particularly, the present teachings relate to an apparatus and a method to reconstruct an anterior cruciate ligament with soft tissue replacements within a femoral tunnel.

BACKGROUND

The statements in this section merely provide background information related to the present disclosure and may not constitute prior art.

The knee joint is frequently the object of injury and is often repaired using arthroscopic surgical procedures. An example of such arthroscopic surgical procedure is the replacement of anterior cruciate ligaments of the knee. The tearing of these ligaments is common in sports activities such as football or skiing.

Currently, fascia lata soft tissue replacements are flexible strands which are affixed to a threaded stud and turned into the femoral tunnel. Unfortunately, this procedure may result in the soft tissue replacement being wrapped upon itself during insertion. Hamstring soft tissue replacements are also currently fixed over a screw in the tibial tunnel and fixed on the lateral femur. This technique requires the femoral tunnel to completely penetrate the femur. In addition, according to present procedures, fixation of the soft tissue replacement on the femoral side requires a large incision.

Further, various other graft portions, such as a patellar tendon graft, which can include a bone tendon bone graft can be used. The graft can be harvested from between patella and the selected bone to which the tendon is anchored. This allows for creation of a bone-tendon-bone graft where the tendon is already anchored to bone portions and only the bone portions are fixed relative to the implant site in the bone. Further examples include a quadriceps tendon graft as various examples of autografts. All grafts from similar sites of selected individuals can also be used in a patient requiring a graft. Further, xenograft materials can be harvested from compatible animals for implantation to selected patients. Also, synthetic materials, such as those that are biologically compatible and include appropriate physical properties can be used. One skilled in the art is generally aware of the various types of graft materials that can be provided for performing a grafting procedure.

It has been difficult to insert and fasten a soft tissue replacement in a blind hole or tunnel. Attempts have been made to thread the soft tissue replacement through the tunnel and over an anchor, but with some difficulty. Thus far, the prior art has not developed a quick and efficient way to implant a soft tissue replacement over an implanted anchoring system.

While offering certain improvements in arthroscopic surgery to repair ligaments, the prior art may still be improved upon to overcome the limitations on the endoscopic hamstring soft tissue replacement fixation due, in many instances, to the weakness of the flexible strand used to span the gap between the tendon soft tissue replacement and the fixation post.

Other techniques attempt to use biological fixation to augment or replace mechanical fixation. While increasing fixation strength these techniques require time to fully realize their fixation potential. Additionally the techniques may take additional surgical time and resources that a purely mechanical fixation technique may not require.

SUMMARY

An apparatus including a member that acts as a flexible strand insertion and guide rod is used to increase the simplicity and effectiveness of a soft tissue implant procedure. The member inserts a flexible strand, which has been preloaded onto the insertion rod, into a blind tunnel formed in a bone structure and provides a guide for a drill point or bit. Thus the member may be removed with the flexible strand already positioned in place to pull an implant into the blind tunnel over the drill point. A cross or set pin is then pulled after the drill point into the drill hole to lock the implant in place.

A first embodiment includes an apparatus to position a flexible strand in a tunnel, having a diameter, formed in a bone while performing a surgery. The apparatus comprises a guide member extending along a first axis and having a first end and second end. The guide member includes a guide portion defining an area, extending from the first end and along the first axis. The guide portion includes a first leg and a second leg, the first leg and the second leg define a slot disposed therebetween, wherein the slot defines a first plane. The first leg further defines a first groove and the second leg defines a second groove; wherein the first groove extends along a distal end of the first leg and along a length of the first leg and the second groove extends along a distal end of the second leg and along a length of the second leg. The first groove and the second groove are adapted to receive the flexible strand. The first groove and the second groove define a second plane. The first plane and the second plane intersect within the area defined by the guide portion.

A second embodiment of the apparatus includes an apparatus to place a flexible strand in a tunnel, having a diameter, formed in bone while performing a surgery. The apparatus comprises a first member having a first end and a second end spaced apart. The first end defines a slot, adapted to guide an instrument, wherein the slot lies in a first plane. The first end further defines a groove, wherein the groove lies in a second plane. The first plane and the second plane intersect. A second member having a first end and a second end, the second member defines a passage positioned adjacent the first end. The first member extends adjacent to the second end of the second member; wherein the first end of the first member and the passage are generally aligned.

A third embodiment includes a kit of surgical devices for performing arthroscopic surgery in tunnels, having a diameter, formed in bones. The kit comprises a guide system comprising a first member comprising a first leg and a second leg, a terminal end of said first leg defining a passage having a first axis. The kit further comprises at least one guide member extending along a second axis having a first end and a second end, wherein the first end extends from a terminal end of said second leg, and wherein the first axis and the second axis are generally orthogonal. Also included is a guide portion extending from the second end of the at least one guide member wherein the guide portion defines an angularly disposed slot and groove. Additionally, a tunnel forming device adapted to form a tunnel in the bone and further adapted to be received through the passage and the slot.

The new apparatus allows a new and unique method of performing an implant procedure. A method of surgically implanting a soft tissue replacement for attaching two bone members comprises inserting an insertion rod having a flexible strand pre-loaded on the insertion rod into a first tunnel. Next, forming a second tunnel transverse and through the first tunnel and the insertion rod with a tool bit. Next, retaining the flexible strand within the first tunnel. The method also includes removing the insertion rod from the first tunnel.

Further areas of applicability of the present teachings will become apparent from the detailed description provided hereinafter. It should be understood that the detailed description and specific examples, while indicating the various embodiments, are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 7 is a perspective view of the soft tissue replacement pulled over the K-Wire and out through the tibial tunnel;

FIG. 8 is a perspective view of the soft tissue replacement in place and the ACL Cross Pin set in place in the transverse tunnel in the femur.

DETAILED DESCRIPTION OF VARIOUS EMBODIMENTS

The following description of various embodiments is merely exemplary in nature and is in no way intended to limit the present teachings, its application, or uses. Moreover, while the present teachings are discussed in detail below with regard to ACL reconstruction, those skilled in the art will recognize the other types of soft tissue fixation may employ the present teachings.

Figure 1:
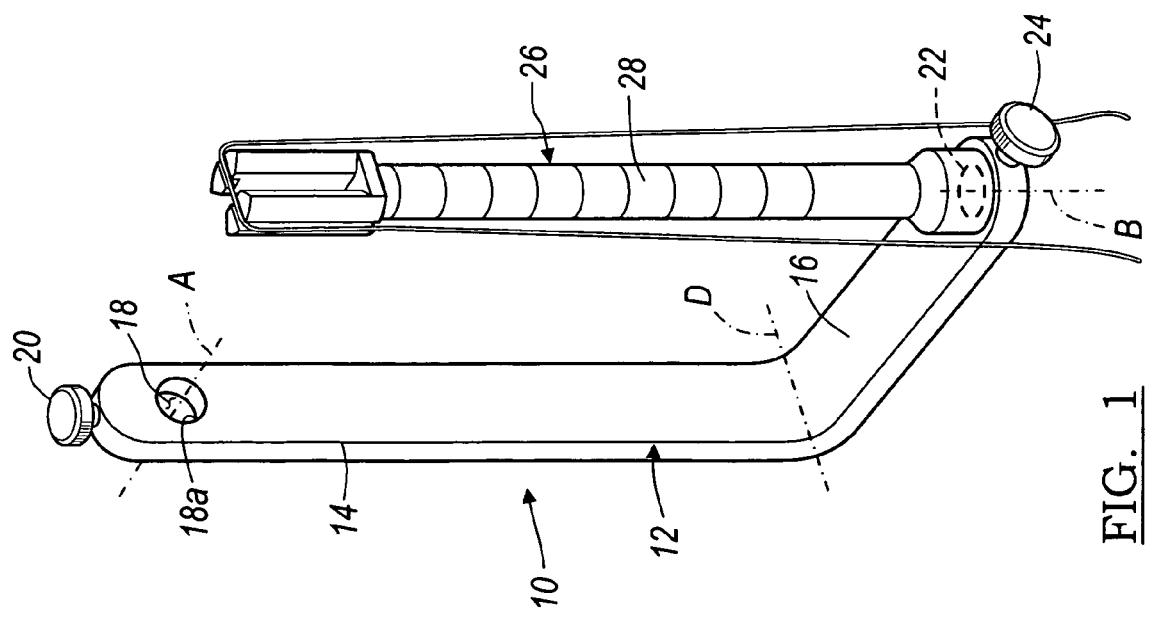
FIG. 1 is a perspective view of the bone insertion rod affixed to a U-Guide.

Referring to FIG. 1, a generally guide apparatus 10 which may be generally a U-shaped guide or a U-Guide generally includes an L-shaped retaining bar or L-guide 12 which includes two portions or legs, a first portion 14 and a second portion 16, that is substantially perpendicular to the first portion 14. The first portion 14 defines a guide section 18, having a guide section ledge 18a, formed transversely through the first portion 14. The guide section may be passage through or transverse to the first portion 14 such as a bore wherein the guide section ledge would be a bore ledge. A set screw 20 is provided to create a locking mechanism for the guide section 18. The second portion 16 defines a bore 22 formed transversely through the second portion 16. Also, a flexible strand notch or flexible strand retaining member 23 is formed near the bore 22 on the second portion 16. A second set screw 24 is also provided to create a locking mechanism for the bore 22. The L-guide 12 is shown in an L-shape, however, it will be understood the L-guide 12 may be any appropriate form. Generally, however, the axes defining the guide section 18 and the bore 22 are orthogonal. Therefore, the first axis A of the guide section 18 should intersect the second axis B of the bore 22 at a right angle at a position.

An insertion or guide rod 26 is adjustably held in the bore 22 and locked in place with the second set screw 24. With continuing reference to FIG. 1 and further reference to FIG. 2, the insertion rod 26 includes a body portion 28. The body portion 28 is substantially cylindrical and formed around a longitudinal axis C. The body portion 28, which is generally a solid, may also taper towards the guide portion 36 (described herein). Also, the body portion 28 may include depth indicia 29 to give a visual indication of the depth of the insertion rod 26 into a patient.

Extending from a first end of the body portion 28 is an L-Guide engaging portion 30 which includes a notch or projection 32 that is received in the second portion 16 of the L-Guide 12 to ensure proper orientation of the insertion rod 26 to the L-Guide 12. The notch 32 on the insertion rod 26 is keyed to be received on to a portion of the second portion 16. The insertion rod 26 further includes a collar 34, having a first shoulder 34a and a second shoulder 34b, to ensure that the insertion rod 26 is held at a predetermined depth in the L-Guide 12 and to further ensure proper orientation of the insertion rod 26 relative to the L-Guide 12.

A guide portion 36 extends from a second end of the body portion 28. The guide portion 36 includes two generally parallel legs 38 and 40 and a shoulder 41. Each leg 38, 40 extends from the body portion 28 along axis C, though offset therefrom. The two legs 38, 40 define a slot 42, where the slot 42 extends substantially the distance of the two legs 38, 40 and has a slot ledge 42a where the two legs 38, 40 meet at the shoulder 41.

Also formed in each of the legs 38, 40 is a flexible strand groove 44. The flexible strand groove 44 may be any appropriate depth, but exemplary is substantially equal in depth to the diameter of a cord or flexible strand thread to be used with the apparatus 10. The flexible strand groove 44 extends, along the outside of each leg 38, 40, substantially the length of the legs 38, 40 and also over the distal end of the legs 38, 40. The flexible strand groove 44 also extends generally along axis C, though offset therefrom, and also over the terminal end of each leg 38, 40. The plane defined by the slot 42 is substantially orthogonal to the plane defined by the flexible strand groove may lie on any relative plane as long as the two planes intersect within the area defined by the guide portion 36. As described herein, a tool may be placed through the slot 42 while a cord is placed over the slot 42 by being positioned in the flexible strand groove 44.

The insertion rod 26 may be any desired length. Preferably, however, the distance between the second collar shoulder 34b and the slot ledge 42a is equal to the distance between a first end of the first portion 14, generally represented by line D, and the guide section ledge 18a. In this way, the guide section ledge 18a and the slot ledge 42a are generally equidistant from the second portion 16. Therefore, any instrument received through the guide section 18 would remain substantially parallel to the second portion 16 when it passed through the slot 42.

The flexible strand groove 44 is placed orthogonally to the slot 42 so that a cord, such as a flexible strand, may be placed in the flexible strand groove 44 to form an enclosed passage for any device that may be placed through the slot 42. In this way, a device such as a K-Wire (described herein), when inserted through the slot 42a has a flexible strand looped over the K-Wire. It will be understood, however, that the flexible strand groove 44 may be formed at any orientation relative to the slot 42 as long as a flexible strand placed in the flexible strand groove 44 will overlay the slot 42.

The notch 32 ensures that the insertion rod 26 is properly oriented with the L-Guide member 12 of the U-guide apparatus 10. In particular, the slot 42 is preferably aligned with the guide section 18. The set screw 24 tightens against the L-Guide engaging portion 30 to ensure that the insertion rod 26 does not move during a surgical procedure. Also, this ensures the proper keyed fit of the notch 32 into the second portion 16 so that the guide section 18 and the slot 42 are properly aligned. This ensures that the instrument received through the apparatus 10 is aligned. It will be understood, however, that any appropriate means may be used to secure the insertion rod 26 to the L-Guide member 12 of the apparatus 10.

Referring to the remaining FIGS. 3-9, an exemplary method for using the apparatus 10, including the insertion rod 26 is described. It will be understood that although the apparatus 10 is described in the use of an Anterior Cruciate Ligament (ACL) replacement, any appropriate surgery may be performed with the apparatus 10 which would require its attributes.

Figure 3:
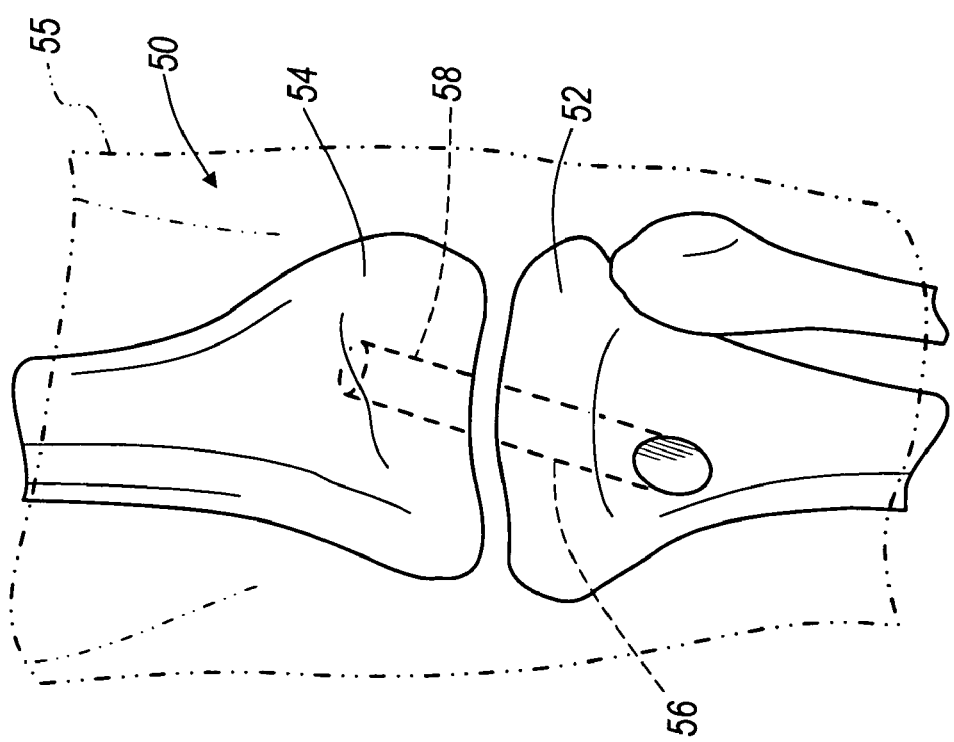
FIG. 3 is an exemplary view of a knee prepared for insertion of the insertion rod.

With particular reference to FIG. 3, a knee 50 generally includes at least a tibia 52 and a femur 54 surrounded by soft tissue 55. The knee 50 is initially prepared by forming a tibial tunnel 56 and a femoral tunnel 58 which are substantially in line with one another such that a straight and solid object could engage both the tibial tunnel 56 and the femoral tunnel 58 without a substantial amount of stress when the knee is placed in flexion between about 30 degrees and 110 degrees. It is understood that incisions must first be made in the soft tissue 55 surrounding the tibia 52 such that a tool may engage the tibia 52 and the femur 54 to form the tibial tunnel 56 and the femoral tunnel 58. Any suitable tool may produce the respective tunnels 56, 58 such as a pneumatic or electric drill or reamer. It is also understood that the femoral tunnel 58 is a blind tunnel. A blind tunnel is a tunnel which includes an entrance but no discernable exit, rather a blind tunnel terminates below the surface of the femur 54.

The size of the tibial tunnel 56 and the femoral tunnel 58 depends upon the size of the soft tissue replacement (described further herein) to be implanted into the patient. The larger the replacement needed, the larger the diameter of the tibial tunnel 56 and the femoral tunnel 58. The tibial tunnel 56 and femoral tunnel 58 may be of any required diameter, but are generally between about 5 and 18 millimeters. It would be understood, however, that if a larger diameter replacement is necessary, then larger diameter tunnels 56, 58 may be produced in the tibia 52 and femur 54 to receive the implant. Additionally, smaller tunnels 56, 58 may be used if only a smaller implant is necessary. In addition, the largest area of the insertion rod 26 will have a diameter substantially equal to the diameter of the tibial tunnel 56 and femoral tunnel 58. For example, if the insertion rod 26 was produced so that the guide portion 36, in particular the shoulder 41, form the largest diameter of the insertion rod 26, then the outside diameter of the guide portion 36 would be substantially equal to diameter of the tibial tunnel 56 and the femoral tunnel 58. Also, the body portion 28 may have a lesser diameter, or a taper towards the shoulder 41, to ease insertion and removal of the insertion rod 26. This ensures that the insertion rod 26, and particularly the slot 42, are substantially centered in the femoral tunnel 58 for the remaining procedure.

Figure 2:
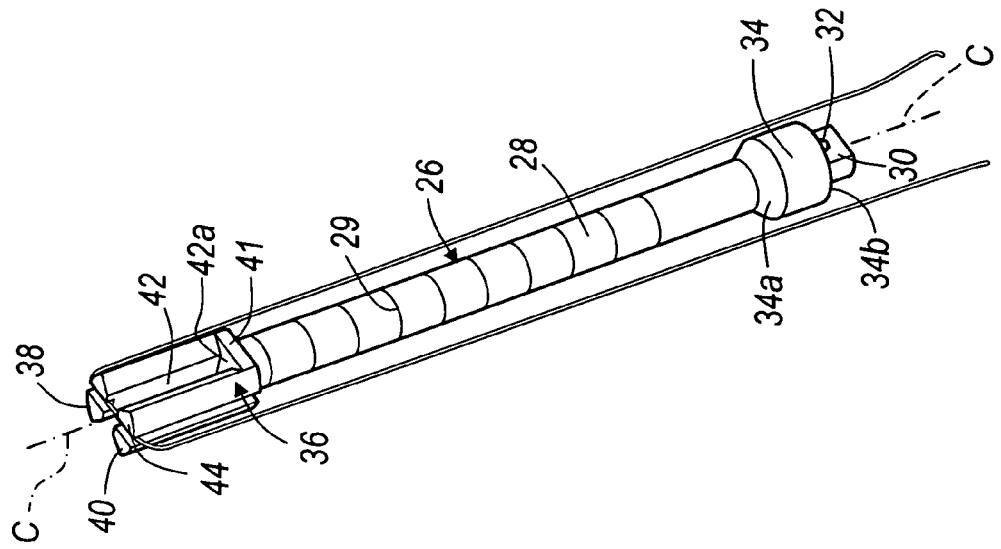
FIG. 2 is a perspective view of bone insertion rod not affixed to the U-Guide.
Figure 4:
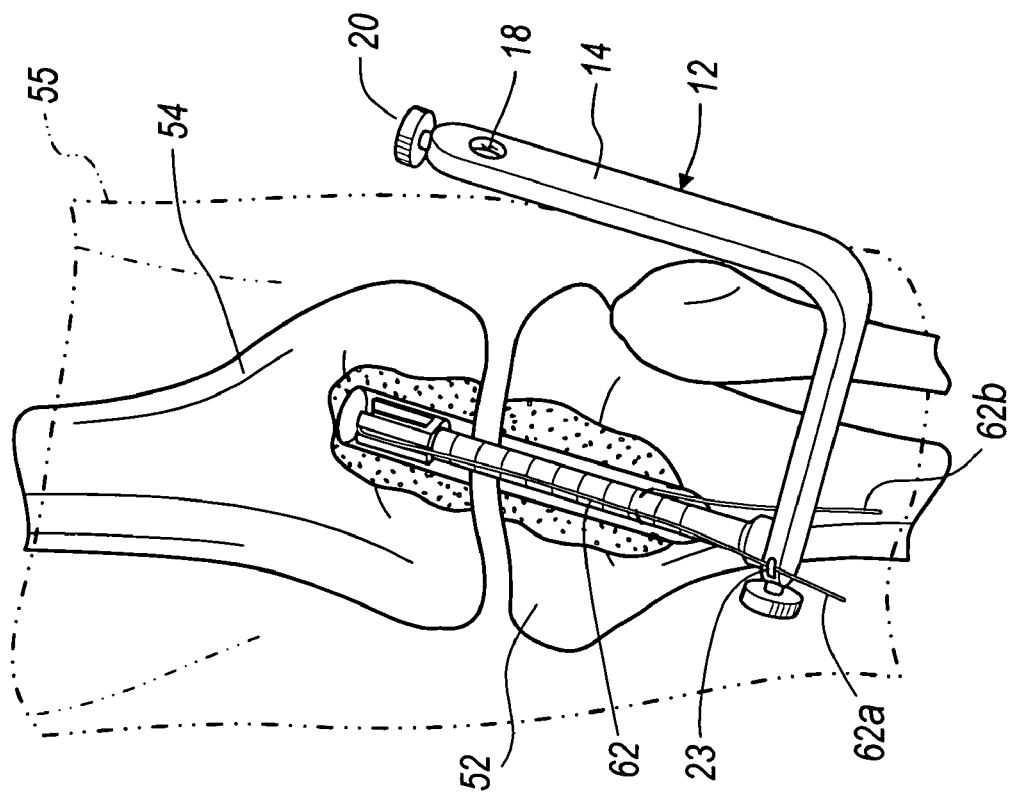
FIG. 4 is a perspective view of the insertion rod and U-Guide inserted into the tibia and femur tunnels with the flexible strand in place.

A flexible strand 62, having a trailing end 62a and a leading end 62b, is placed or pre-loaded into the flexible strand groove 44 and then the insertion rod 26 is inserted through the tibial tunnel 56 and into the femoral tunnel 58, as best shown in FIG. 4 (see also FIGS. 1 and 2). The flexible strand 62 may be any generally known strand suitable to the purpose such as a mono- or poly-filament suture, a flexible wire, or cord made of any suitable material. The flexible strand groove 44 allows the flexible strand 62 to be inserted through the tunnels 56, 58 without engaging the walls of the tunnels 56, 58. Generally the depth of the flexible strand groove 44 is at least equal to the diameter of the flexible strand 62. The flexible strand 62 is placed so that it reaches substantially to the end of the femoral tunnel 58 and the slot 42 creates an opening through the center of the femoral tunnel 58 through which an instrument may pass, while not interrupting the flexible strand 62 which has been inserted into the femoral tunnel 58 by the insertion rod 26. The flexible strand 62 is caught in the flexible strand notch 23. The flexible strand 62 is held in position during the insertion of the insertion rod 26 into the tunnels 56, 58 and during the remaining surgical procedure by the flexible strand notch 23. Any suitable means may be used to hold the flexible strand 62 in place relative to the L-Guide member 12 of the apparatus 10. The flexible strand notch 23, which holds the flexible strand 62 with friction, is merely exemplary of one appropriate means to hold the flexible strand 62 in place.

Once the insertion rod 26 has been inserted into the femoral tunnel 58, so that the flexible strand 62 is positioned properly, a device, such as a drill bit or point 70 is used to produce a transverse tunnel 72 in the femur 54. The transverse tunnel 72 is formed transversely to the femoral tunnel 58. The transverse tunnel 72 will include an insertion point 72a and an exit point 72b. It will be understood that an incision must first be made in the soft tissue 55 surrounding the femur 54, so that the drill bit or point 70 may engage the femur 54 to form the transverse tunnel 72. The drill point 70 may be powered by any appropriate device known in the art such as an electric or pneumatic drill. Furthermore, additional guide units or bullets 74, such as the U-Guide bullet produced by Arthotek, Inc. of Warsaw, Ind., may be used to ensure the proper orientation and depth of the drill point 70. The guide bullet 74 is inserted into the guide section 18 and held in place with the set screw 20 to ensure the drill point 70 is properly aligned with the slot 42 when producing the transverse tunnel 72. The transverse tunnel 72 is produced through the entire width of the femur 54 so that the drill point 70 exits the femur 54 producing the exit point 72b. This allows the drill point 70 to be removed through the exit point 72b at the appropriate time. While the apparatus 10 is still in place, a cannulated reamer (not shown) enlarges a portion of the transverse tunnel 72. The reamed tunnel 73 receives the pin 84 (described herein). The reamed tunnel 73 does not extend the length of the transverse tunnel 72.

Figure 6:
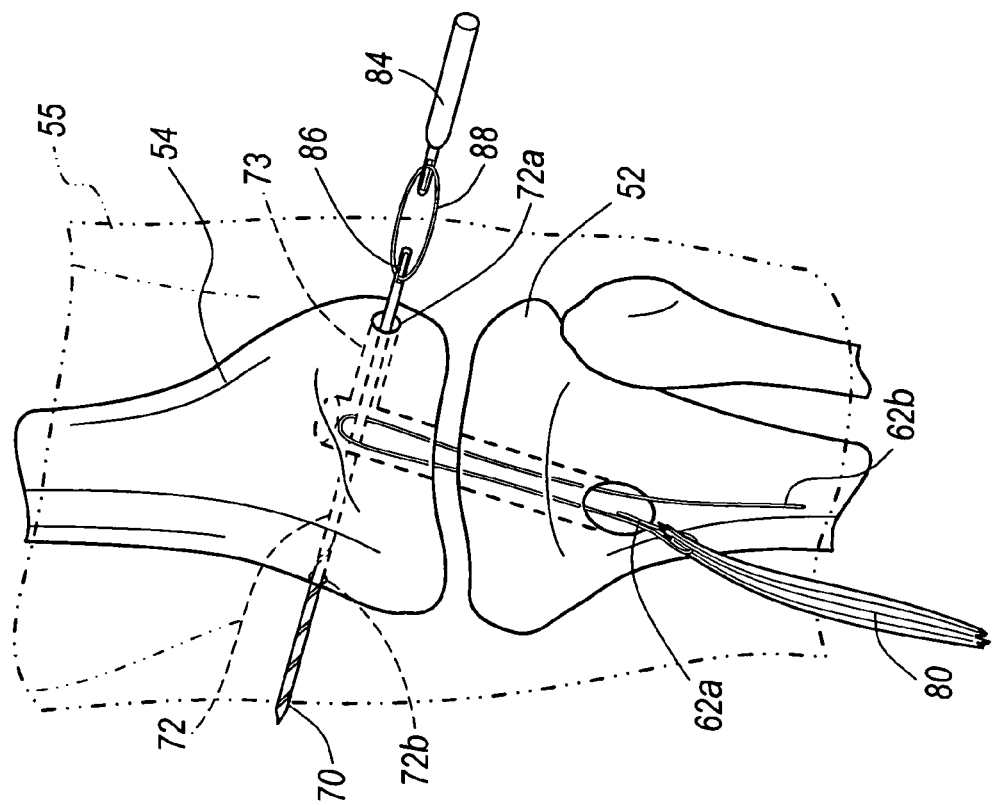
FIG. 6 is perspective view of the K-Wire Drill Point with the flexible strand affixed to a soft tissue replacement and draped over the K-Wire Drill Point.
Figure 5:
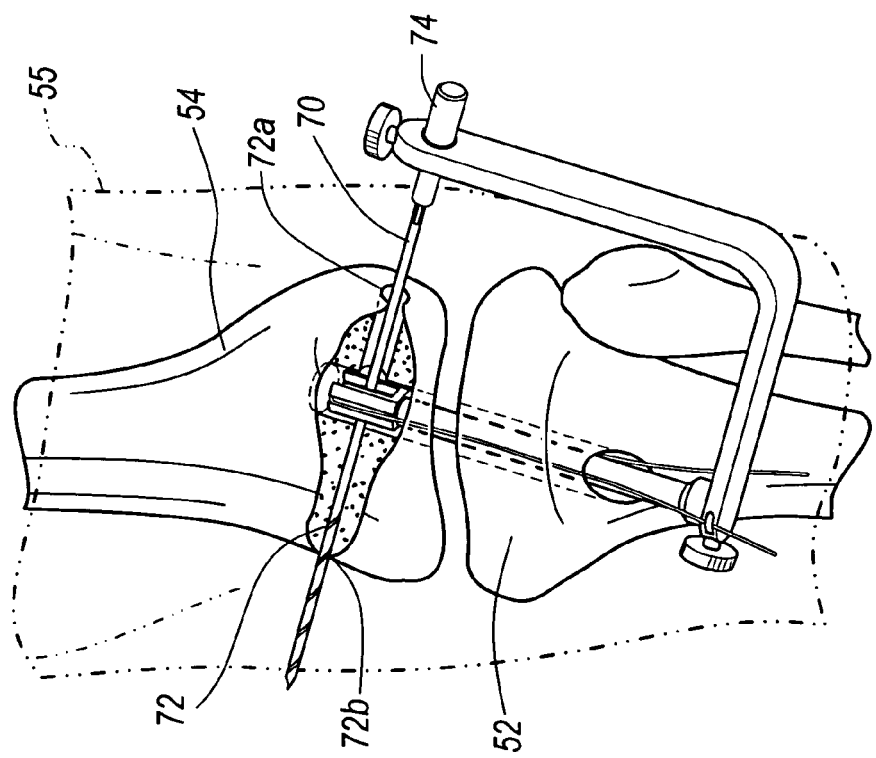
FIG. 5 is a view of the U-Guide and insertion rod in place with a K-Wire Drill Point forming a transverse tunnel.

After the reamed tunnel 73 is produced, the apparatus 10, is removed as particularly shown in FIG. 6. Once the apparatus 10 has been removed, the drill point 70 remains in the transverse tunnel 72. A soft tissue replacement 80 is affixed to the trailing end 62a of the flexible strand 62. The soft tissue replacement may be any suitable replacement such as a hamstring portion, an allograft tissue replacement, a xenograft tissue replacement, or an artificial soft tissue replacement which may be produced from materials such as polymers or metal. After the soft tissue replacement 80 has been affixed to the trailing end 62a, the leading end 62b of the flexible strand 62 is pulled drawing the soft tissue replacement 80 first through the tibial tunnel 56 and then through the femoral tunnel 58 over the drill point 70 and back down the femoral tunnel 58 and out through the tibial tunnel 56. This produces a loop of the soft tissue replacement 80 over the drill point 70 inside of the femoral tunnel 58. After being looped over the drill point 70, the two free ends 80a and 80b of the soft tissue replacement 80 extend from the tibial tunnel 56 adjacent to the tibia 52.

After the soft tissue replacement 80 has been looped over the drill point 70, an ACL cross pin or pin 84 is pulled into place in the reamed tunnel 73. The drill point 70 generally includes an eyelet 86 which will allow the attachment of the pin 84 to the drill point 70. Generally, the pin 84 is attached to the eyelet 86 through a second flexible strand 88 or other appropriate means. After the pin 84 is attached to the eyelet 86, the drill point 70 is pulled through the transverse tunnel 72, through the loop of the soft tissue replacement 80 and out the exit point 72b. This pulls the pin 84 into position and fixes it within the transverse tunnel 72, as particularly shown in FIG. 8. Once the pin 84 has been fixed in place in the transverse tunnel 72, the attached flexible strand 88 may be cut or otherwise disengaged from between the eyelet 86 and the pin 84. The drill point 70 is then freely removed from the transverse tunnel 72. This leaves the pin 84 lodged into the transverse tunnel 72 which may be locked in place with either portions of the pin 84 or through any other appropriate locking means. Although any appropriate means may be used to hold pin 84 in the reamed tunnel 73, the pin 84 may include a square end to hold pin 84 in place. The pin 84 may also be threaded such as the device described in U.S. Pat. No. 5,674,224 entitled "Bone Mulch Screw Assembly For Industrial Fixation of Soft Tissue Soft tissue replacements And Method For Using Same" to Stephen M. Howell et al. incorporated herein by reference.

Figure 9:
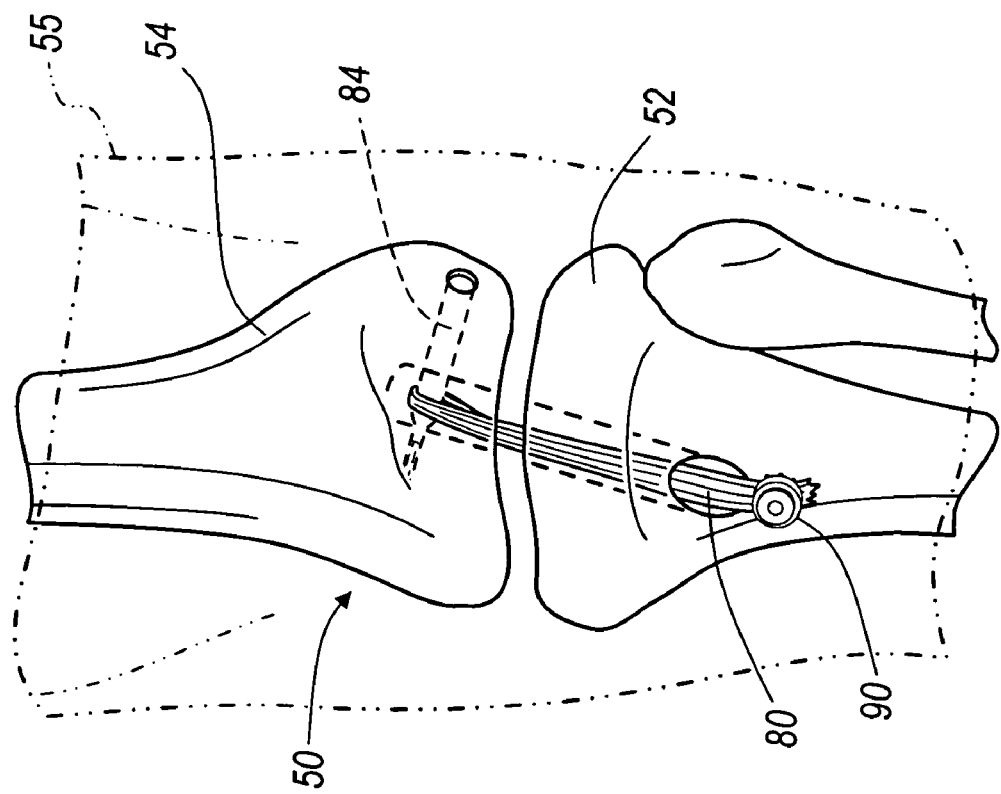
FIG. 9 is a deep view of the knee with an ACL replacement having its free ends affixed to the tibia and the femoral end affixed over the ACL Cross Pin.

Because the pin 84 has been lodged in the transverse tunnel 72, and the soft tissue replacement 80 is looped over the pin 84, only the free ends 80a and 80b need to be secured to the tibia 52 to complete the implantation. A staple 90 is used to affix the free ends 80a and 80b of the soft tissue replacement 80 to the tibia 52, as best shown in FIG. 9. It will be understood, however, that any appropriate means may be used to affix the free ends 80a, 80b to the tibia 52 such as U.S. Pat. No. 5,674,224 entitled "Bone Mulch Screw Assembly For Industrial Fixation of Soft Tissue Soft tissue replacements And Method For Using Same" to Stephen M. Howell et al.; U.S. Pat. No. 6,280,472 B1 entitled "Apparatus And Method For Tibial Fixation Of Soft Tissue" to James A. Boucher et al.; and U.S. Pat. No. 5,931,869 entitled "Apparatus And Method For Tibial Fixation Of Soft Tissue" to James A. Boucher et al. each incorporated herein by reference. Once the free ends 80a and 80b of the soft tissue replacement 80 are affixed to the tibia 52, the soft tissue replacement 80 securely attaches the tibia 52 and the femur 54 substantially as a natural ACL would.

It will be understood that any appropriate means may be used to affix the soft tissue replacement 80 in the femoral tunnel 58. The pin 84 is merely exemplary of any appropriate device to affix the soft tissue replacement 80 in the femoral tunnel 58. Any commonly known screw or other fixation device may be used to fix the soft tissue replacement 80 in the femoral tunnel 58. It will also be understood that the soft tissue replacement 80 may be pulled over the pin 84 after the pin 84 has been lodged in the transverse tunnel 72. In particular, if the pin 84 is smooth, the soft tissue replacement 80 may be pulled over the pin 84 without damaging the soft tissue replacement 80 itself. The drill point 70 is simply removed from the transverse tunnel 72 before the soft tissue replacement 80 is pulled into the femoral tunnel 58.

It will also be understood that the method for performing the described procedure may be altered but remain within the scope of the present teachings. For example the flexible strand 62 may looped over the insertion rod 26 such that the two free ends 62a and 62b are on one side and a loop of the flexible strand is formed on the other side of the insertion rod 26. Thus the soft tissue replacement 80 may be affixed to both free ends 62a and 62b or placed through the loop and then pulled over the insertion rod 26.

The description is merely exemplary in nature and, thus, variations that do not depart from the gist thereof are intended to be within the scope of the present teachings. Such variations are not to be regarded as a departure from the spirit and scope of the present teachings.

What is claimed is:

1. A system to position a flexible strand in a tunnel formed in a bone, the system comprising:

a guide member extending along a first axis and having a first end and second end; and a guide portion extending from said first end and along said first axis, said guide portion including, a first leg having a first groove and a second leg having a second groove, said first leg and said second leg separate and defining a slot therebetween;

a first surface defined by an end of said first leg, wherein said first groove has a first groove portion formed in said first surface, the first groove portion defined by two side walls and a back wall and a second groove portion formed in an exterior side surface of said first leg, the second groove portion defined formed by two side walls and a back wall, wherein said first groove portion and said second groove portion are connected; and a second surface defined by an end of said second leg, wherein said second groove has a third groove portion formed in said second surface, the third groove portion defined by two side walls and a back wall and a fourth groove portion formed in an exterior side surface of said second leg, the fourth groove portion defined by two side walls and a back wall, wherein said third groove portion and said fourth groove portion are connected;

wherein said slot is transverse to both said first groove and said second groove;

wherein said guide portion with said first groove and said second groove are configured to position the flexible strand in the tunnel formed in the bone.

2. The system of claim 1, further comprising:

a guide system comprising a first member and a second member positioned at approximately a right angle, wherein a first bore is formed at a terminal end of said first member and a second bore is formed at a terminal end of said second member;

said second end of said guide member is adapted to be received in said first bore; and wherein said slot and said second bore are generally aligned;

wherein said guide system is configured to be exterior to the bone when said guide portion is positioned in said tunnel to position the flexible strand in the tunnel in the bone.

3. The system of claim 2, further comprising a tunnel forming device adapted to be received through said second bore and said slot, wherein a tunnel formed by said tunnel forming device is generally aligned with said slot and said second bore.

4. The system of claim 3, wherein said second end includes an alignment system comprising:
 a projection extending laterally from said second end; and
 a collar extending cylindrically from said guide member and disposed between said first end and said projection.

5. The system of claim 4, wherein said second bore includes a detent adapted to receive said projection in a keyed manner.

6. The system of claim 1, wherein said slot has a depth greater than a depth of said first and second grooves into said respective said first leg and said second leg.

7. The system of claim 1, wherein said first groove and said second groove both have internal dimensions substantially equivalent to external dimensions of said flexible strand and said first groove and said second groove are both formed into said guide portion and are aligned across said slot.

8. The system of claim 1, wherein the tunnel defines a diameter and said guide portion has a width substantially equal to the diameter of the tunnel in the bone.

9. The system of claim 8, wherein the internal dimensions of said first groove and said second groove are substantially equal to the dimensions of the flexible strand to contain the flexible strand within a perimeter of the first leg or the second leg so that said flexible strand does not engage a wall of the tunnel.

10. The system of claim 1, wherein the flexible strand is held over said slot and in said first groove and said second groove.

11. The system of claim 1, further comprising a guide system comprising a first member and a second member positioned at approximately a right angle, wherein a passage is formed at a terminal end of said first member and said second end of said guide member extends from a terminal end of said second member, and wherein said slot and said passage are generally aligned.

12. The system of claim 11, further comprising a tunnel forming device adapted to be received through said passage and said slot, wherein a tunnel formed by said tunnel forming device is generally aligned with said slot and said passage.

13. The system of claim 1,
further comprising:
 a slot ledge extending between said first leg and said second leg;
 wherein said slot defines a first plane and both said first groove and said second groove define a second plane, such that said first plane and said second plane intersect within said slot.

14. A system to position a flexible strand in a tunnel formed in a bone, the system comprising:
 a guide assembly comprising:
  a first member configured to be external to the bone comprising a first leg and a second leg, a terminal end of said first leg defining a guide section having a first axis;
  a guide member extending along a second axis having a first end and a second end, wherein said first end extends from a terminal end of said second leg, and wherein said first axis and said second axis are generally orthogonal; and
  a guide portion extending from said second end of said guide member wherein said guide portion defines an angularly disposed slot and groove having a first groove portion formed in a flat end of said guide portion on a first side of said slot, a second groove portion formed in said flat end of said guide portion on a second side of said slot, a third groove portion formed in a first exterior side of said guide portion, and a fourth groove portion formed in a second exterior side of said guide portion, wherein said groove is a blind groove having a solid back wall formed in the guide portion; and
 a tunnel forming device adapted to form a cross tunnel in the bone at least by being received through said guide section and passing through said slot;
 wherein said guide portion is configured to be positioned in the tunnel in the bone when said first member and is external to the tunnel.

15. The system of claim 14, further comprising a flexible strand, wherein said flexible strand is selectively received in said groove.

16. The system of claim 15, wherein the depth of said groove is substantially equivalent to an exterior dimension of said flexible strand.

17. The system of claim 16,
 wherein said first groove portion and said third groove portion are connected;
 wherein said second groove portion and said fourth groove portion are connected;
 wherein said groove is adapted to hold said flexible strand over said tunnel forming device while said tunnel forming device is received through said slot.

18. The system of claim 17, wherein said slot and said guide section are generally aligned.

19. The system of claim 17, further comprising a first implant to hold the soft tissue replacement in the tunnel.

20. The system of claim 19, further comprising a second implant to affix the soft tissue replacement adjacent the bone.

21. The system of claim 14, wherein said slot has a depth greater than a depth of said groove.

22. The system of claim 14, wherein said guide member is selected from a plurality of guide members wherein each of said plurality of guide members have guide portions with different exterior dimensions, wherein said exterior dimensions are substantially equal to a diameter defined by the tunnel.

23. The system of claim 14, wherein said slot and said groove are disposed generally orthogonally.

24. The system of claim 14, wherein said first leg and said second leg are substantially perpendicular.

25. The system of claim 14, wherein said guide section is a bore, and wherein a terminal end of said second leg defines a second bore having a third axis comprising a detent, wherein said first axis and said third axis are generally orthogonal.

26. The system of claim 25, wherein said first end of said guide member comprises:
 a projection adapted to be received in said detent; and
 a collar including a shoulder adapted to engage said second leg such that said guide portion is a predetermined distance from said second leg.

27. A system to position a flexible strand in a tunnel formed in a bone, the system comprising:
 an insertion rod comprising a guide portion operable to be positioned in a first tunnel of the bone and having a slot separating a first leg and a second leg with a slot ledge that extends between the first leg and the second leg, a first flexible strand receiving groove formed in the first leg, a second flexible strand receiving groove formed in the second leg such that a flexible strand is operable to be positioned within an external side surface and an end surface of the respective first leg and the second leg of the insertion rod and over the slot;

a flexible strand pre-loaded on the guide portion and in the first flexible strand receiving groove and the second flexible strand receiving groove;

an external guide member defining a guide section interconnected with the insertion rod and positioned exterior to the bone when the insertion rod is positioned in the first tunnel;

a tunnel forming device operable to be aligned through the guide section of the external guide member, wherein the tunnel forming device is operable to form a second tunnel in the bone through a portion of the first tunnel; and a retaining device operable to be positioned in the formed second tunnel and through the slot under the flexible strand pre-loaded on the insertion rod;

wherein the flexible strand can be retained within the first tunnel with the retaining device.

28. The system of claim 27, wherein the tunnel forming device is operable to be aligned via the external guide member relative to the guide portion of the insertion rod.

29. The system of claim 28, wherein said first flexible strand receiving groove and said second flexible strand receiving groove are formed transverse to said a slot.

30. The system of claim 29, further comprising:
a keyed portion of the insertion rod; and
a keyed portion and an external guide portion of said external guide;
wherein the keyed portion of the insertion rod and the keyed portion of the external guide member are operable to assist in assuring alignment of the guide portion and the external guide portion.

31. The system of claim 27, the retaining member and the tunnel forming device are the same device.

32. The system of claim 27, wherein the tunnel forming device is a drill point.

33. A system to position a flexible strand in a tunnel formed in a bone, the system comprising:
a first member having a first end and a second end spaced apart, said first end having:
a slot between a first leg and a second leg with a slot ledge extending between said first leg and said second leg, wherein said slot is adapted to guide an instrument and said slot lies in a first plane,
a first groove formed in said first leg of said first end having a first blind groove portion connected to a second blind groove portion that extends from said first end towards said second end on an exterior side wall of said first leg; and
a second groove formed in said second leg of said first end having a third blind groove portion connected to a fourth blind groove portion that extends from said first end towards said second end on an exterior side wall of said second leg;
wherein said first groove and said second groove are configured to position the flexible strand in the tunnel formed in the bone;
wherein said first groove and said second groove lie in a second plane and said first plane and said second plane intersect in the slot,
a second member having a first end and a second end, said second member defining a guide section positioned adjacent said first end and said first member extends adjacent to said second end of said second member; wherein said first end of said first member and said guide section are generally aligned.

34. The system of claim 26, wherein said second end of said second member defines a bore comprising a detent.

35. The system of claim 34, wherein said second member further comprises an alignment system comprising:
a projection extending laterally from said second end keyed to said detent; and
a collar extending cylindrically from said member and disposed between said first end and said projection.

36. The system of claim 35, further comprising a flexible strand positionable in said first groove and said second groove, wherein said flexible strand is slideable in said first groove and said second groove.

37. The system of claim 36, further comprising a tunnel forming device adapted to be received through said guide section and said slot.

38. The system of claim 37, where said second member is L-shaped.

39. The system of claim 38, wherein said guide section is a bore defined at said first end and substantially aligned with said slot;
wherein said tunnel forming device is operable to move through said slot and under the flexible member positioned in said groove.

* * * * *